US009593933B2

(12) United States Patent
Oritz Egea et al.

(10) Patent No.: US 9,593,933 B2
(45) Date of Patent: Mar. 14, 2017

(54) METHOD FOR CALIBRATING AND CORRECTING THE SCANNING DISTORTION OF AN OPTICAL COHERENCE TOMOGRAPHY SYSTEM

(75) Inventors: Sergio Oritz Egea, Madrid (ES); Susana Marcos Celestino, Madrid (ES); Damian Siedlecki, Madrid (ES); Carlos Dorronsoro Díaz, Madrid (ES)

(73) Assignee: CONSEJO SUPERIOR DE INVESTIGACIONES CIENTIFICAS (CSIC), Madrid (ES)

( * ) Notice: Subject to any disclaimer, the term of this patent is extended or adjusted under 35 U.S.C. 154(b) by 714 days.

(21) Appl. No.: 14/114,254

(22) PCT Filed: Mar. 21, 2012

(86) PCT No.: PCT/ES2012/070185
§ 371 (c)(1),
(2), (4) Date: Dec. 19, 2013

(87) PCT Pub. No.: WO2012/146811
PCT Pub. Date: Nov. 1, 2012

(65) Prior Publication Data
US 2014/0107960 A1     Apr. 17, 2014

(30) Foreign Application Priority Data
Apr. 29, 2011    (ES) .................. 201130685

(51) Int. Cl.
*G01C 19/00*    (2013.01)
*G01D 18/00*    (2006.01)
(Continued)

(52) U.S. Cl.
CPC ............ *G01B 9/0209* (2013.01); *A61B 3/102* (2013.01); *A61B 5/0066* (2013.01); (Continued)

(58) Field of Classification Search
CPC .................. A61B 3/102; A61B 5/0066; A61B 2560/0233; G06T 5/006; G06T 7/0018; (Continued)

(56) References Cited

U.S. PATENT DOCUMENTS

| | | | |
|---|---|---|---|
| 5,005,578 A | 4/1991 | Greer et al. | |
| 7,884,945 B2 * | 2/2011 | Srinivasan | A61B 3/102 356/479 |
| 2003/0118227 A1 | 6/2003 | Winsor et al. | |

FOREIGN PATENT DOCUMENTS

JP        2005-261487        9/2005

OTHER PUBLICATIONS

International Search Report issued Aug. 2, 2012 in International (PCT) Application No. PCT/ES2012/070185.
(Continued)

*Primary Examiner* — An Do
(74) *Attorney, Agent, or Firm* — Wenderoth, Lind & Ponack, L.L.P.

(57) ABSTRACT

Method for calibrating and correcting the scanning distortion of any optical coherence tomography system by using reference patterns and obtaining mathematical relationships between the positions of the reference points in a reference pattern and the local coordinates of said reference points, said coordinates are obtained by means of said optical coherence tomography system.

10 Claims, 3 Drawing Sheets

(51) Int. Cl.
  *G01B 9/02* (2006.01)
  *A61B 3/10* (2006.01)
  *A61B 5/00* (2006.01)
  *G06T 5/00* (2006.01)
  *G06T 7/00* (2006.01)
(52) U.S. Cl.
  CPC ...... *G01B 9/02072* (2013.04); *G01B 9/02076* (2013.01); *G01B 9/02091* (2013.01); *G06T 5/006* (2013.01); *G06T 7/0018* (2013.01); *A61B 2560/0233* (2013.01); *G01B 2290/65* (2013.01); *G06T 2207/10101* (2013.01)
(58) Field of Classification Search
  CPC ...... G06T 2207/10101; G01B 9/02076; G01B 9/0209; G01B 9/02072; G01B 9/02091; G01B 2290/65
  USPC ............................ 702/85, 104; 356/479, 497
  See application file for complete search history.

(56) References Cited

OTHER PUBLICATIONS

Ortiz, S. et al.: "Optical distortion correction in Optical Coherence Tomography for quantitative ocular anterior segment by three-dimensional imaging", Optical Express, Feb. 1, 2010, vol. 18, No. 3, pp. 2782-2796.

Borja, D. et al.: "Distortions of the posterior surface in optical coherence tomography images of the isolated crystalline lens: effect of the lens index gradient", Biomedical Optical Express, Dec. 1, 2010, vol. 1, No. 5, pp. 1331-1340.

Westphal, V. et al.: "Correction of geometric and refractive image distortions in optical coherence tomography applying Fermat's principle", Optical Express, May 6, 2002, vol. 10, No. 9, pp. 397-404.

\* cited by examiner

METHOD FOR CALIBRATING AND CORRECTING THE SCANNING DISTORTION OF AN OPTICAL COHERENCE TOMOGRAPHY SYSTEM

OBJECT OF THE INVENTION

The present invention, as formulated in this descriptive specification, refers to a method for calibrating and correcting the scanning distortion of optical coherence tomography systems.

The present invention improves the optical coherence tomography technique, since the method described in the invention allows obtaining a two-dimensional and three-dimensional quantitative tomography of surfaces based on optical coherence tomography images. The method may be applied to any optical coherence tomography system wherein the scanning system of the tomography system is based on a 2-axis scanning system.

The present invention constitutes an improvement on the state of the art, since it allows quantifying images obtained using optical coherence tomography techniques and to obtain topographical maps of general surfaces and more specifically, of ocular surfaces, thereby being more advantageous than alternative existing techniques.

The present invention thereby aims to provide a method for correcting the scanning distortion of any optical coherence tomography system by using reference patterns and obtaining mathematical relationships between the positions of the reference points in a reference pattern and the local coordinates of said reference points obtained by means of said optical coherence tomography system.

In general, the present invention refers to the field of image capturing systems and in particular, to optical coherence tomography systems.

INVENTION BACKGROUND

Optical coherence tomography or OCT (Huang, D. et al., 1991. Optical coherence tomography. Science 254: 1178-1181) is an interferometric technique, which allows obtaining the differences in optical path between surfaces. Using a lateral sweep scanner on a sample allows obtaining a collection of interferograms (A-scans), which form an image of the cross-section of the sample (B-scan). Scanning in both directions (x and y) allows obtaining a collection of B-scans and constructing a three-dimensional image of the sample. The axial resolution of the technique is in the order of microns (Povazay, B. et al. 2002. Submicrometer axial resolution optical coherence tomography. Opt. Lett. 27:1800) and is determined by the spectral bandwidth of the source (superluminescent diodes are typically used, although femtosecond lasers or swept-source lasers are also used). The interferograms may be obtained in the temporal domain, physically changing the length of the reference arm or, in the frequency domain, especially (spatial frequency domain (Fercher A. F. et al., "Measurement of Infraocular Distances by Backscattering Spectral Interferometry". Optics Communications, 1995, 117:43-48)) or temporarily (temporal frequency domain (Chinn, S. R. et al., (1997). Optical coherence tomography using a frequency-tunable optical source. Opt. Lett., 22, 340-342)) codified by means of a spectrometer or scanning the frequency of the source.

The increased velocity with which data are acquired in the OCT systems (of up to 150,000 A-scans/s) has allowed the capture of three-dimensional images in less than 1 second. The high axial resolution (2-20 µm) and high lateral resolution (in the region of 100 µm) give optical coherence tomography high potential for topographical and profilometric characterization of surfaces and for the in vivo measurement of the corneal topography, amongst other things.

In the current state of the art (relative to optical coherence tomography techniques, ocular surface topography systems and profilometric techniques for general surfaces based on other methods), there is a need to quantify optical coherence topography systems, in order to improve the ocular biometry obtained by means of these systems and to therefore achieve a new, advantageous process associated with the use of profilometry based on optical coherence tomography. Furthermore, there is a need for a general method for calibrating optical coherence tomography systems, with the aim of improving the quantitative information obtained from these systems. In general, the use of the optical coherence tomography (OCT) technique as a topographical technique is limited by the presence of scanning distortion associated with the architecture of the sweep system (generally formed by a 2-axle mirror scanner), which also produces field distortion and astigmatism in the images. The main factor contributing to this distortion is the separation of the mirrors in the scanner and the focal length of the lens that collimates the beam on the sample and, to a lesser extent, the flatness of the mirrors and misalignment of the rotation beam of the mirrors.

Up until now, it remains unknown for the state of the art a general method for calibrating and correcting the scanning distortion which may be applied to any optical coherence tomography system without prior knowledge of the optical and mechanical configuration of the system. The absence of calibration and correction of the scanning distortion has prevented the quantitative use of the optical coherence tomography systems from becoming generalized, as well as the correct interpretation of topographical data. One of the main aims of the present invention is to provide a method for calibrating and correcting the scanning distortion in order to quantify the topographical data obtained using any Optical Coherence Tomography system. Correcting optical distortion is relatively simple in optical coherence tomography systems based on one single scanner and with two-dimensional acquisition of data. However, in systems with two scanners, with three dimensional acquisition of data, distortion is complex since it is not linear and has dependencies between the lateral and axial positions, as well as being dependent on the optical and geometrical configuration of each piece of equipment. This complexity has generally prevented quantitative three-dimensional topographical data from being obtained.

Various optical coherence tomography systems for the anterior segment of the eye exist on the market. These systems provide quantitative biometric data, generally in the axial direction. Nevertheless, the correction of the scanning distortion in these commercial systems has not been proven, as is the case in one of the most widespread previous commercial systems (Visante, Zeiss) based on Placido rings, despite it providing three-dimensional corneal elevation data. Some authors provide alternative scanning configurations that minimize scanning distortion depending on the mirror configuration of the same (Chin et al, (1997). Optical coherence tomography using a frequency-tunable optical source. Opt. Lett., 22, 340-342) or in scanner systems oriented towards cutting machines (Ireneusz Grulkowski et al, "Anterior segment imaging with Spectral OCT system using a high-speed CMOS camera", OPT. Express 17, 4842-4858, (2009)). However, these systems always leave residual distortions, which should be corrected in order to be able to obtain the three-dimensional coordinates of each point of a surface.

Westphal et al., (Correction of geometric and refractive image distortions in optical coherence tomography applying Fermat's principle, Opt. Express 10, 397-404, (2002)) provides a solution to the scanning distortion in corneal OCT systems wherein the scanning system is a non-linear scanner system (with resonant mirrors with non-telecentric scanning), by means of axially taking images around the axial position, applying only to two-dimensional sections of the sample and not to three-dimensional ones.

Kim et al., (Automated analysis of OCT images of the crystalline lens, Proc. SPIE 7163, 716313, (2009)) use a telecentric system to acquire transversal (two-dimensional) images free of optical distortion. O'hara and Meyer (U.S. Pat. No. 7,878,651) propose the use of beams perpendicular to the cornea in order to obtain the refraction thereof. However, this does not produce the claimed distortion correction but rather it produces the opposite effect, as the beams have to transverse very different paths.

Ortiz et al. (Optical coherence tomography for quantitative surface topography, Appl. Opt. 48, 6708-6715, (2009)) proposed a method for optimizing the scanning distortion in a temporal domain OCT system as well as for three-dimensional correction of residual scanning distortion, based on acquiring axial images by means of a confocal lateral image channel built into the OCT system. However, this method requires the use of a confocal channel to obtain the scanning distortion. This confocal channel is not generally available in Optical Coherence Tomography instruments, which is why the method is not generally applicable. These authors furthermore provide theoretical estimations of the scanning distortions, which allow predicting the scanning distortion measured experimentally but these require precise knowledge of the optical and geometrical configuration of the instrument. The theoretical estimations allow obtaining an optimal configuration which in turn allow minimizing these distortions but not to eliminate them, it being necessary to carry out the proposed method for the residual distortions which remain in the optical illumination and light collection system.

The scanning distortion correction method, object of the present invention, may be applied to obtaining the profilometry of surfaces in general or specifically to corneal topography, by means of employing optical coherence tomography systems.

U.S. Pat. No. 7,416,300 describes the use of optical coherence tomography for metrology of lenses and surfaces but it does not mention the correction of the scanning distortion. U.S. Pat. No. 716,313 and U.S. Pat. No. 5,491,524 describe corneal topographic mapping systems by means of optical coherence tomography but they do not disclose the correction of the scanning distortion. Generally speaking, in these studies, the maps are obtained based on a set of cross-sections acquired by an assembly of meridians around a rotation shaft, centered in the corneal apex (in a similar way to Scheimpflug systems or crack rotation scanning systems), limiting the lateral resolution in the radial dimension.

Once the scanning distortion has been corrected, the optical coherence tomography technique is advantageous in comparison to surface contact profilometry (for example Talysurf), including faster data acquisition and the absence of contact with the sample. It is also more advantageous than optical profilometry based on microscopy, including greater operational distance, much faster data acquisition in wider areas and greater independence in terms of the specular reflection properties of the sample. Once the scanning distortion has been corrected, the optical coherence tomography technique is advantageous in terms of measuring corneal topography in patients, in comparison to corneal video keratoscopy based on Placido rings, usually employed in clinics, including greater axial and lateral resolution, in the radial dimension and the direct acquisition of elevation data, without suppositions derived from the presence of the skew ray. It is also more advantageous than corneal topography based on Scheimpflug, including faster acquisition and greater axial and lateral resolution.

DESCRIPTION OF THE INVENTION

In order to fulfill the objectives and avoid the limitations set out above, the invention consists of a method for calibrating any kind of optical coherence tomography system.

The method of the present invention is proposed as a calibration protocol for any optical coherence tomography system for obtaining quantitative topographical maps based on three-dimensional optical coherence tomography images of the sample. The method allows correcting distortion in any optical coherence tomography system, independently of its specific optical and geometric configuration, in comparison to other methods described, which are limited to one particular configuration of the system or to two-dimensional images or they adopt a hypothesis that requires previous knowledge of the system, including the arrangement of the elements thereof and the system alignment and response. The present invention approaches the empirical measurement of system scanning distortion, determining, via use of a reference pattern, the distortion of the spatial coordinates of the volume in question.

The present invention makes use of a reference pattern, which may consist of, although it is not limited to, a calibrated grating mounted on a linear axial displacement device, a transparent bucket with a three-dimensional sculpted grating or a staircase pattern.

The present invention makes use of optical coherence tomography images of said reference pattern, from which the positions are extracted in the image of the reference points in the pattern, thereby making it possible to establish a relationship between the resulting measurements taken by the optical coherence tomography instrument.

In general, the relationship will be established between discrete points of the pattern, for example nodes in a grating for each axial position or nodes in a three-dimensional grating and the positions of the reference pattern points in the data obtained by the optical coherence tomography system, expressed in local coordinates of the system. The relationship is generalized to any position of the volume in the calibrated area by means of the interpolation, which is generally non linear, of the data between the points sampled, by means of analytic or numerical functions with a sample of points which is sufficiently dense. For example, the distorted horizontal and vertical lines of a calibration grating formed by equally spaced nodes joined together by straight lines may be adjusted to quadric functions (lateral coordinates) and the axial positions of the nodes by means of a linear regression (direction cosines). Said analytic functions allow representing the position of any point of the distorted volume in local coordinates. The present invention establishes a mathematical transformation of coordinates between the distorted volume, in the local coordinates of the system and the real volume of the reference pattern or equivalently, of the magnitude of the scanning distortion for each point, in general, in angular coordinates. The present invention establishes a mathematical transformation of coordinates between the distorted volume, in the local coordinates of the system and the real volume of the reference pattern. The scanning distortion will be corrected by means of applying this transformation to all the points of any image acquired by the Optical Coherence Tomography system.

In one embodiment of the invention, the method is applied to optical coherence tomography images directly, in grey scale. These images are processed by means of digital algorithms in order to eliminate noise from the image and surface segmentation.

In another embodiment of the invention, the method is applied to previously segmented points of the surface.

In a further embodiment of the invention, the method is applied to analytic functions adjusted to the edges or surfaces of the image.

In one embodiment of the invention, the method is applied to the image of any reflective surface, obtained by means of any optical coherence tomography system with a 2-axle sweep scanner.

In an additional embodiment of the invention, the method is applied to the anterior corneal surface, obtained by means of any optical coherence tomography system with a 2-axle anterior segment sweep scanner.

In a further embodiment of the invention, the method is applied to the entire image of the anterior segment of the eye, obtained by means of any optical coherence tomography system with a 2-axle anterior segment sweep scanner.

In another embodiment of the invention, the method is applied to the entire image of the anterior segment, obtained by means of any optical coherence tomography system with a 2-axle retina sweep scanner.

Therefore, the present invention claims a scanning distortion of an optical coherence tomography system, which comprises the following phases:
  i) selecting a reference pattern which comprises a number of known reference points, which are described in real coordinates;
  ii) acquiring images from the reference pattern selected in phase i), this reference pattern being located in an object space of the optical coherence tomography system, by means of the optical coherence tomography system;
  iii) identifying, in the images acquired from the reference pattern, a number of positions of a number of reference points described in local coordinates provided by the optical coherence tomography system and which correspond to the reference points selected in phase i);
  iv) obtaining a mathematical distortion relationship which defines a transformation between the local coordinates provided by the optical coherence tomography system and real coordinates, the mathematical relationship being based on the comparison of the positions of the reference points known in the local coordinates in phase iii) and in the real coordinates of phase i) and;
  v) correcting the distortion by means of applying the mathematical distortion relationship obtained in phase iv) to the data obtained by the optical coherence tomography system.

In a preferred embodiment of the invention, the mathematical distortion relationship described in phase iv) comprises being an interpolation of the positions of the reference points, by means of functions selected from analytic functions, numerical functions and a combination of both.

In another embodiment of the invention, the reference pattern of phase i) is selected from any two-dimensional mobile structure with marks located in known positions and any three-dimensional structure with marks located in known positions.

In a further embodiment of the invention the reference pattern of phase i) is selected from:
  a three-dimensional calibration grating, the known reference points being the nodes of the three-dimensional calibration grating.
  A two-dimensional calibration grating mounted on a linear calibrated displacement element, the known reference points being the nodes of the calibration grating in distinct axial positions;
  A cube with a three-dimensional sculpted calibration grating, the known reference points being the nodes of the three-dimensional calibration grating and;
  A staircase pattern, the known reference points being the abrupt in depth transitions between steps.

In yet another embodiment of the invention, the reference points described by means of the local coordinates in phase iii) are joined by means of lines, these lines being defined by analytic functions. In order to carry out the calibration of the system, the points identified in phase iii) of the method are joined together by lines. Owing to the scanning distortion, the lines which join them, in any of the three axes of the space, do not follow conventional analytic functions. For example, in a specific embodiment, the analytic functions correspond to parabolic functions, given that these parabolas simulate the curves described by the lines that join the points identified in phase iii) of the method.

Furthermore, the use of the method described in the present specification has been proposed for obtaining scanning distortion data which has been calibrated and corrected with the optical coherence tomography system, selected from:
  Two-dimensional section data;
  Three-dimensional volume data;
  Corneal topographical data;
  Retinal topographic data;
  Data of the internal surfaces of an eye, in combination with a compensation of an optical distortion and of a refraction;
  Image data of the anterior segment of the eye;
  Image data of the layers of the retina;
  Signal data obtained in a photo-detector of the optical coherence tomography system;
  Intensity image and volumes data:
  Mapped points data corresponding to a number of edges previously extracted from an optical coherence tomography image and;
  Data on surfaces adjusted to a number of edges previously extracted from an optical coherence tomography image.

Nevertheless, there are many other possible uses for the object of the present invention, in many fields of science which have not been specified in the present descriptive specification.

Please note that the scanning distortion is of the variety which allows tackling other kinds of corrections, such as correcting the optical distortion, once said scanning distortion has been corrected by means of the process described, this optical distortion being that which is produced upon seeing a surface through another surface.

DESCRIPTION OF VARIOUS EXAMPLE EMBODIMENTS OF THE INVENTION

Below is a description of various example embodiments of the invention, which serve as a non-limiting description thereof, with reference to the numbering adopted in the figures introduced above.

Therefore, below is a description of a preferred calibration method for an optical coherence tomography system and its application for measuring a plastic surface and a patient's cornea.

The method has been applied to OCT images obtained by means of a spectral Optical Coherence Tomograph of an anterior, non-commercial camera in a research lab. The device employed comprises a system of scanners x-y (8 mm aperture and 13.6 mm of separation between the centre of the mirrors) and a 75 mm collimating-focusing lens. The light source is a superluminescent diode (840 nm, 50 nm spectral width).

The delay line is formed by a spectrometer with a diffraction network and a CMOS camera. The acquisition velocity is 25,000 A-scans (interferograms per second).

Figure 1:
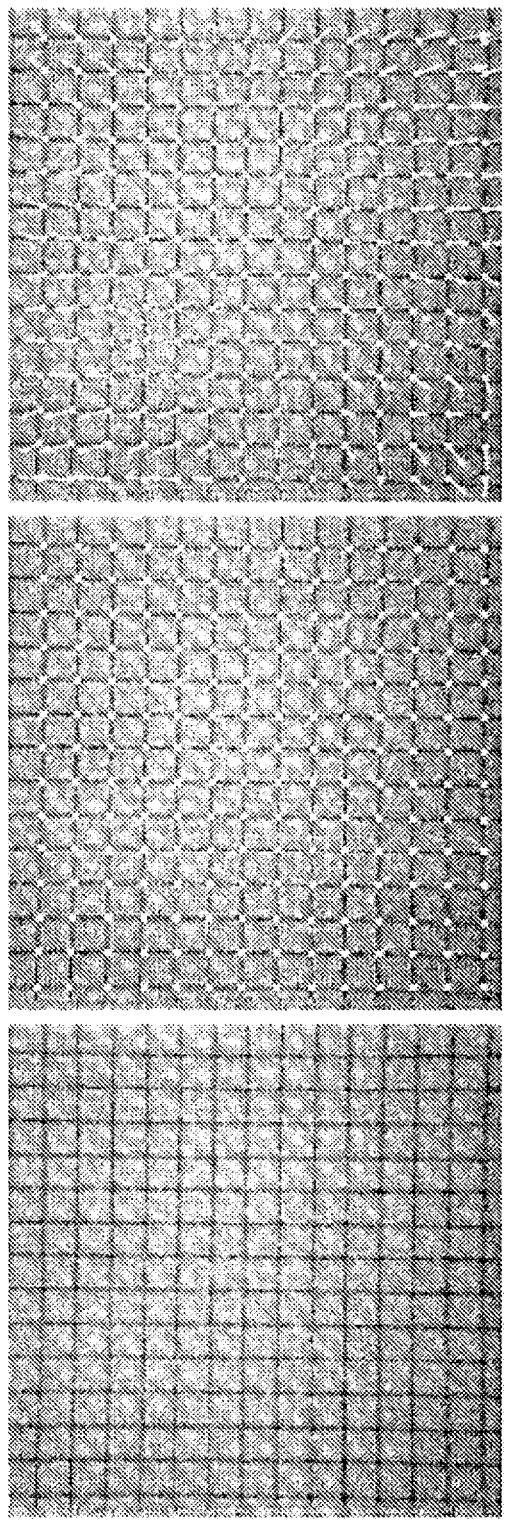
FIG. 1a.—Is an integrated image of a grating as a reference pattern.
FIG. 1b.—Represents the grating shown in the FIG. 1a, with the nodes being marked.
FIG. 1c.—It shows the grating shown in FIGS. 1a and 1b with the nodes and the estimate of the real lateral coordinates marked out.

The process described in the invention is applied following the stages below:

(1) Producing a reference pattern, consisting of a flat reflective opaque surface with known printed or recorded spacing and especially in a graduated calibration mesh or grating printed on white paper with black ink;

(2) Manual or automatic displacement with graduation, upon which said calibration grating is placed;

(3) Acquiring 3D volumes of the calibration grating placed in the sample position (object space) and in various axial positions around said position, in a range of 7 mm and steps of 0.5 mm. FIGS. 1a, 1b and 1c show images of the embodiments of the grating used to calibrate the scanning distortion. FIG. 1a represents the calibration grating when it is employed, whilst FIG. 1b represents the same grating, wherein the known nodes are identified by white points. The FIG. 1c represents the grating with identified nodes and the displacement of said nodes owing to the scanning distortion. As you can see from looking at these figures, the scanning distortion has caused the nodes to be displaced, this displacement being represented by the lines originating from the original positions of the nodes to the position in which they are found after images have been taken in the object space of the optical coherence tomography system;

(4) Obtaining integrated two-dimensional images of the calibration grating, for each axial position, based on the total of the signal of each A-scan;

(5) Eliminating the scanning noise from the image by means of digital filters;

(6) Extracting the edges of the line of the grating by means of image analysis methods, especially by means of a Hough transformation.

(7) Adjusting the quadric functions of the horizontal and vertical lines extracted;

(8) Obtaining the points of intersection of the horizontal and vertical curves and labeling said nodes for each grating image acquired in a different axial position. Therefore, for each node a set of three-dimensional points is obtained, expressed in the local coordinates of the device, for example pixels in the three-dimensional images;

(9) Obtaining a calibration factor between local coordinates of the device (calculated according point 8) and Euclidean coordinates. The Euclidean axial coordinate is obtained from the axial positions of the linear displacements;

(10) Obtaining analytic functions which represent the positions of any point of the image of the calibration grating by means of bicubic interpolation between the estimated positions of the nodes (lateral coordinates) and by means of a linear regression of the axial positions of the nodes (direction cosines);

(11) Obtaining the transformation functions between the real coordinates and the coordinates of the image, or equivalently, of the magnitude of scanning distortion obtained for each point, in angular coordinates and;

(12) Correcting the distortion of a generic point, carried out by means of applying the transformation function of coordinates to each point of the image of a surface obtained by means of the optical coherence tomography system. The scanning distortion magnitude for each point is subtracted (in angular coordinates) from the difference in optical path obtained as an OCT signal for each point of the surface detected, in order to obtain the current position of the surface without distortion.

For the OCT system used in the example, the average scanning distortion is 24 pixels (86 µm) in the horizontal direction ad 7 pixels (24 µm) in the vertical direction, for an angular range of the scanner of between −7.5 and 7.5 degrees.

In the application of the example described, the method is applied to three-dimensional data of a spherical PMMA (polymethyl methacrylate) surface and of a cornea of a patient. Image processing and surface segmentation routines were used for eliminating noise. The method is used for each point of the surface detected in the three-dimensional image. The images are acquired on a 10×10 mm area, with a density of 200×200 A-scans in the case of the spherical PMMA surface and 10×12 mm, with a density of 120×50 A-scans in the case of the cornea of the patient.

The PMMA surface will consist of an aspherical surface treated with a refractive surgery laser (myopic ablation model), which altered the form of the surface, increasing its corneal asphericality. As a reference, the topography of the surface was evaluated with a non-contact profilometer based on confocal microscopy (PLµ, Sensofar).

Figure 2A:
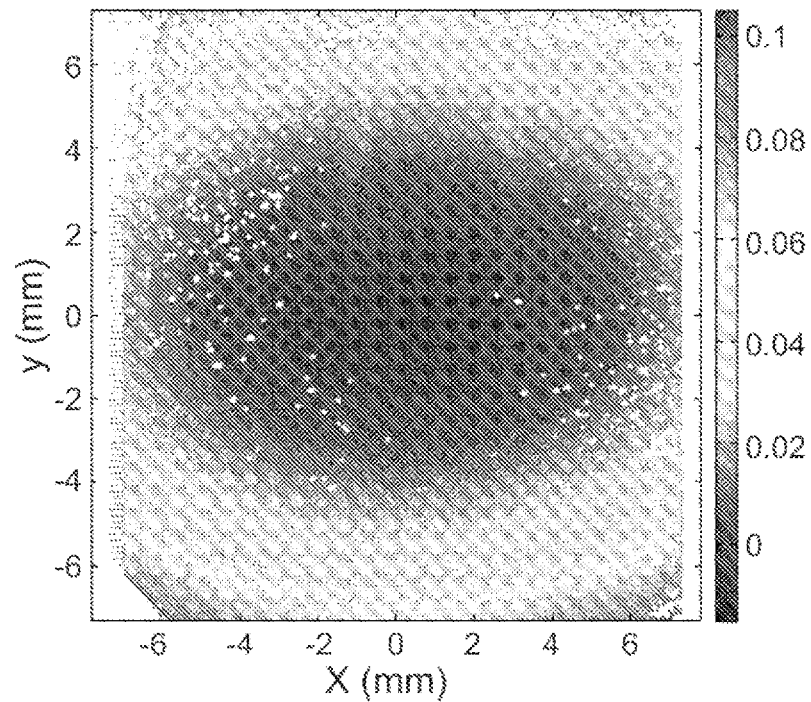
FIG. 2a.—Shows the difference between the real topography (measured by means of profilometry) of a spherical surface and the topography based on OCT without optical distortion correction.
Figure 2B:
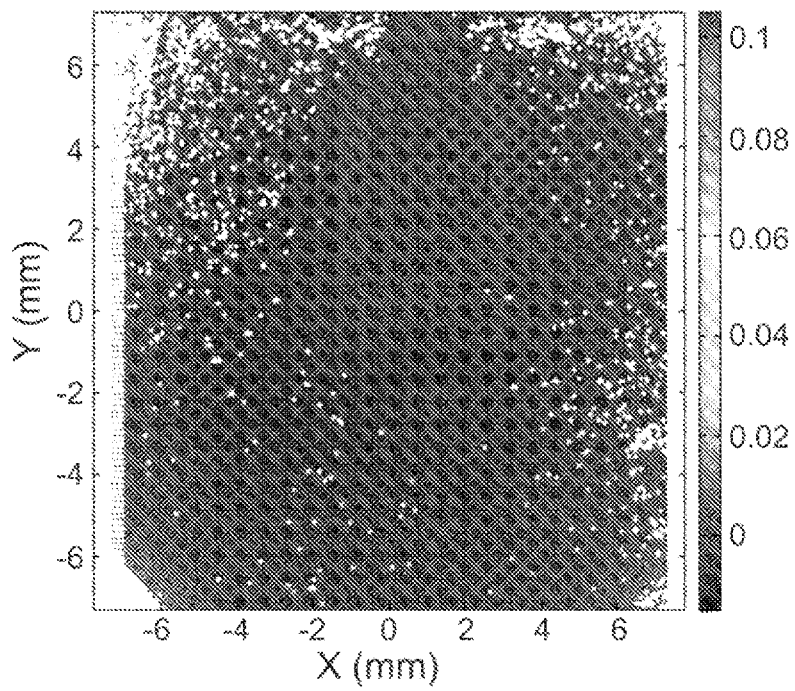
FIG. 2b.—Shows the difference between the real topography (measured by means of profilometry) of as spherical surface and topography based on OCT with correction of the geometrical distortion applied.

The method described in the invention, with the parameters detailed in the application example, was applied to the three-dimensional OCT image acquired on this surface. The topographical data (of the profilometer and the OCT, crude data and following calibration/correction of the scanning distortion) were adjusted to biconical functions (characterised by the radius of the curvature and the asphericality) and to order 8 Zernike polynomials. The discrepancy in the curvature radius adjusted to the OCT surface without calibration or correction relative to the adjustment of the non-contact profilometric profile was 4.6%, whilst the discrepancy after calibration was 1.6%. The discrepancy in the asphricality reduced from 130% to 5%. FIG. 2a shows the map of difference between the surface and the adjustment of the profilometric profile before calibration and FIG. 2b shows the map of difference between the surface and the adjustment of the profilometric profile after the application of the calibration method, object of the present invention.

Figure 3A:
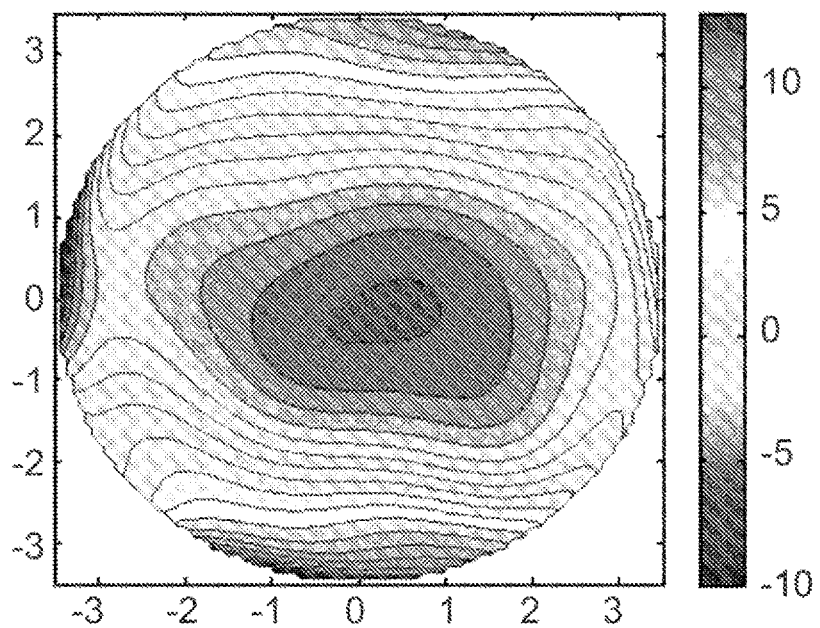
FIG. 3a.—Is a topographical map of the anterior face of the cornea of a patient obtained by means of OCT prior to applying the scanning distortion correction.
Figure 3B:
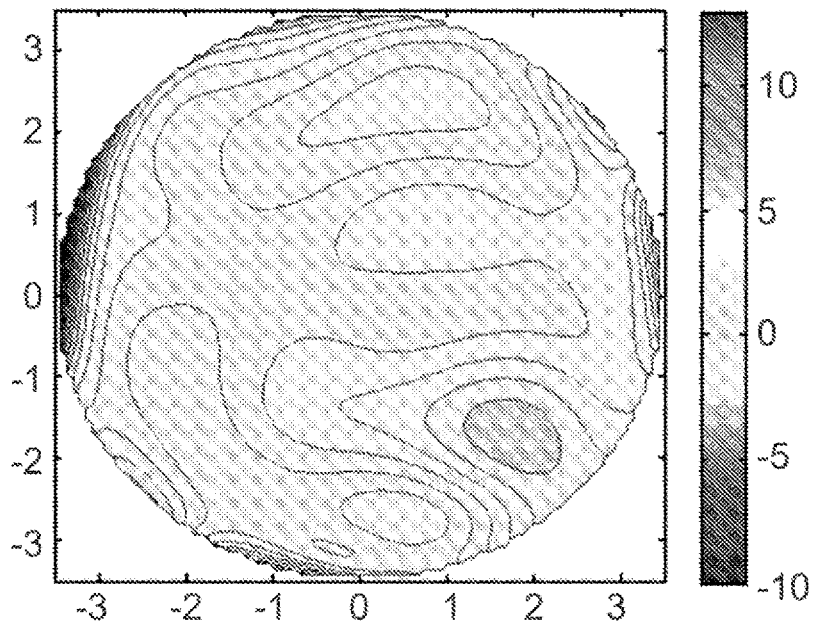
FIG. 3b.—Is a topographical map of the anterior face of the cornea of a patient obtained by means of OCT after having applied the scanning distortion correction.

For another example embodiment in which the method, object of the invention, was applied to the cornea of a human being, the patient measured was a normal young subject. The subject fixated his vision on a stimulus which allows aligning the keratometric papillary axis with the optical axis of the instrument. The OCT image acquisition time is 0.72 seconds. The method described in the invention, with the parameters described in the application example, was applied to the three-dimensional OCT image acquired from the anterior corneal face. The topographical data was adjusted to biconical surfaces and to order 8 Zernike polynomials. The correction of scanning distortion reduced the asymmetry of the surface by 5.7% (curvature radius) and 9.5% (asphericality). The apical radius of curvature of the cornea before and after correction was 7.38 and 7.59 mm, respectively and the asphericality −0.38 and −0.42, respectively. FIG. 3a shows the topographical map of the anterior face of the cornea (adjustment to Zernike polynomials) of a patient obtained by means of OCT, before applying the scanning distortion correction and FIG. 3b shows said topographic map of the anterior face of the cornea after having applied the scanning distortion correction, in both cases, with prior subtraction of the greater sphere.

The invention claimed is:

1. A method for calibrating and correcting scanning distortion of an optical coherence tomography system, wherein the method comprises the following phases:
  i) selecting a 3-D reference pattern which comprises a number of known reference points which are described in a number of real 3-D coordinates;
  ii) acquiring 3-D images of the reference pattern selected in phase i), the reference pattern being located in an object space of the optical coherence tomography system, by means of the optical coherence tomography system, the optical coherence tomography system providing the 3-D images by obtaining axial images of a sample at different lateral positions achieved by a lateral scanning of the sample;
  iii) identifying, in the images acquired of the reference pattern, a number of positions of a number of reference points described in a number of local 3-D coordinates provided by the optical coherence tomography system, which correspond to the reference points known in phase i);
  iv) obtaining a mathematical distortion relationship which defines a transformation between the local 3-D coordinates provided by the optical coherence tomography system and a number of real 3-D coordinates, the mathematical relationship being based on the comparison of the positions of the known reference points in the local 3-D coordinates of phase iii) and in the real 3-D coordinates in phase i); and
  v) correcting the distortion by means of applying the mathematical distortion relationship obtained in phase iv) to the data obtained by the optical coherence tomography system.

2. The method for calibrating and correcting the scanning distortion of an optical coherence tomography system, according to claim 1, wherein the mathematical distortion relationship of phase iv) is an interpolation of the positions of the reference points, by means of functions selected from analytic functions, numerical functions and a combination of both.

3. The method for calibrating and correcting the scanning distortion of an optical coherence tomography system, according to claim 2, wherein data obtained by calibrating and correcting the scanning distortion of the optical coherence tomography system is selected from:
  two-dimensional section data;
  three-dimensional volume data;
  corneal topography data;
  retinal topography data;
  data on the internal surfaces of an eye in combination with a compensation of an optical distortion and of refraction;
  Image data on an anterior segment of the eye;
  image data on the layers of the retina;
  data on signals obtained in a photo-detector of the optical coherence tomography system;
  intense image and volume data;
  data of maps of points corresponding to a number of edges previously extracted from an image; and
  data on surfaces adjusted to a number of edges previously extracted from an optical coherence tomography image.

4. The method for calibrating and correcting the scanning distortion of an optical coherence tomography system, according to claim 1, wherein the 3-D reference pattern of phase i) is selected from any two-dimensional mobile structure with marks located in known positions and any three-dimensional structure with marks located in known positions.

5. The method for calibrating and correcting the scanning distortion of an optical coherence tomography system, according to claim 4, wherein data obtained by calibrating and correcting the scanning distortion of the optical coherence tomography system is selected from:
  two-dimensional section data;
  three-dimensional volume data;
  corneal topography data;
  retinal topography data;
  data on the internal surfaces of an eye in combination with a compensation of an optical distortion and of refraction;
  Image data on an anterior segment of the eye;
  image data on the layers of the retina;
  data on signals obtained in a photo-detector of the optical coherence tomography system;
  intense image and volume data;
  data of maps of points corresponding to a number of edges previously extracted from an image; and
  data on surfaces adjusted to a number of edges previously extracted from an optical coherence tomography image.

6. The method for calibrating and correcting the scanning distortion of an optical coherence tomography system, according to claim 1, wherein the 3-D reference pattern of phase i) is selected from:

a three-dimensional calibration grating, the known reference points being the nodes of the three-dimensional calibration grating;
a two-dimensional calibration grating mounted onto a calibrated displacement linear element, the known reference points being the nodes of the calibration grating in different axial positions;
a cube with a three-dimensional sculptured calibration grating, the known reference points being the nodes of the three-dimensional calibration grating; and
a staircase pattern, the known reference points being the abrupt in depth transitions between steps.

7. The method for calibrating and correcting the scanning distortion of an optical coherence tomography system, according to claim 6, wherein data obtained by calibrating and correcting the scanning distortion of the optical coherence tomography system is selected from:
two-dimensional section data;
three-dimensional volume data;
corneal topography data;
retinal topography data;
data on the internal surfaces of an eye in combination with a compensation of an optical distortion and of refraction;
Image data on an anterior segment of the eye;
image data on the layers of the retina;
data on signals obtained in a photo-detector of the optical coherence tomography system;
intense image and volume data;
data of maps of points corresponding to a number of edges previously extracted from an image; and
data on surfaces adjusted to a number of edges previously extracted from an optical coherence tomography image.

8. The method for calibrating and correcting the scanning distortion of an optical coherence tomography system, according to claim 1, wherein the reference points described by means of the local coordinates in phase iii) are joined by means of lines, these lines being defined by analytic functions.

9. The method for calibrating and correcting the scanning distortion of an optical coherence tomography system, according to claim 8, wherein data obtained by calibrating and correcting the scanning distortion of the optical coherence tomography system is selected from:
two-dimensional section data;
three-dimensional volume data;
corneal topography data;
retinal topography data;
data on the internal surfaces of an eye in combination with a compensation of an optical distortion and of refraction;
Image data on an anterior segment of the eye;
image data on the layers of the retina;
data on signals obtained in a photo-detector of the optical coherence tomography system;
intense image and volume data;
data of maps of points corresponding to a number of edges previously extracted from an image; and
data on surfaces adjusted to a number of edges previously extracted from an optical coherence tomography image.

10. The method for calibrating and correcting the scanning distortion of an optical coherence tomography system, according to claim 1, wherein data obtained by calibrating and correcting the scanning distortion of the optical coherence tomography system is selected from:
two-dimensional section data;
three-dimensional volume data;
corneal topography data;
retinal topography data;
data on the internal surfaces of an eye in combination with a compensation of an optical distortion and of refraction;
Image data on an anterior segment of the eye;
image data on the layers of the retina;
data on signals obtained in a photo-detector of the optical coherence tomography system;
intense image and volume data;
data of maps of points corresponding to a number of edges previously extracted from an image; and
data on surfaces adjusted to a number of edges previously extracted from an optical coherence tomography image.

* * * * *